Figure 1:
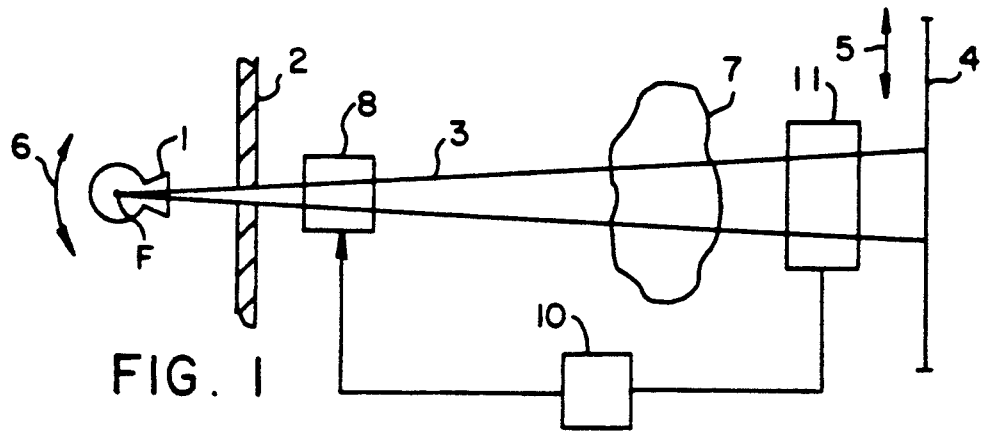

United States Patent [19]
van Elburg et al.

[11] Patent Number: 5,257,305
[45] Date of Patent: Oct. 26, 1993

[54] SLIT RADIOGRAPHY DEVICE PROVIDED WITH ABSORPTION ELEMENTS, AND PROCEDURE FOR PRODUCING ABSORPTION ELEMENTS

[75] Inventors: Hendrik J. van Elburg, Haarlem; Frederik J. Boelens, Delft; Gijsbertus G. Nouwen, Bosschenhoofd, all of Netherlands

[73] Assignee: 38 BV Optische "De Oude Delft, Delft, Netherlands

[21] Appl. No.: 981,238

[22] Filed: Nov. 25, 1992

Related U.S. Application Data

[60] Division of Ser. No. 852,682, Mar. 17, 1992, abandoned, which is a continuation of Ser. No. 613,498, Oct. 31, 1990, Pat. No. 5,134,642.

[30] Foreign Application Priority Data

Jun. 22, 1988 [NL] Netherlands ............. 8801589

[51] Int. Cl.$^5$ ............................................. G21K 5/10
[52] U.S. Cl. ................................. 378/146; 378/145
[58] Field of Search ......................... 378/146, 145

[56] References Cited

U.S. PATENT DOCUMENTS 4,856,040 8/1989 Geluk ..................... 378/146

*Primary Examiner*—Craig E. Church
*Attorney, Agent, or Firm*—Louis E. Marn

[57] ABSTRACT

A slit radiography device scans a body under examination with a fan shaped X-ray beam. A number of absorption elements placed next to each other can be moved into the X-ray beam to a greater or lesser extent in order to influence the X-ray radiation incident on the body per sector of the X-ray beam.

As seen in the longitudinal direction of the slit the absorption elements are designed such that a certain distance is present between them. As seen in the direction of the X-ray radiation the thickness of the material of the absorption elements is always the same, i.e. there are no gaps between the absorption elements that the X-ray radiation can shine through.

3 Claims, 5 Drawing Sheets

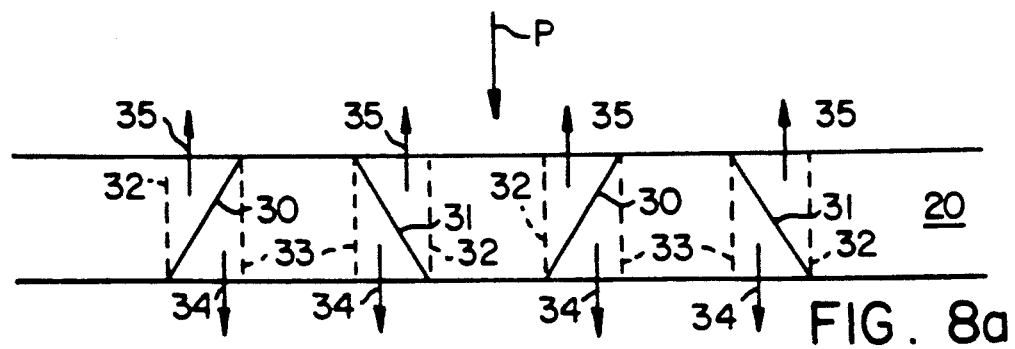
FIG. 8a
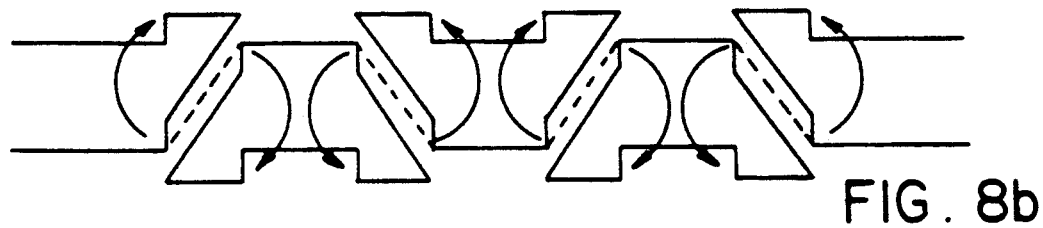
FIG. 8b
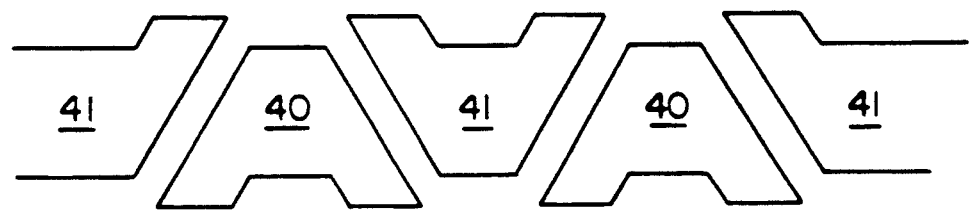
FIG. 8c
FIG. 9
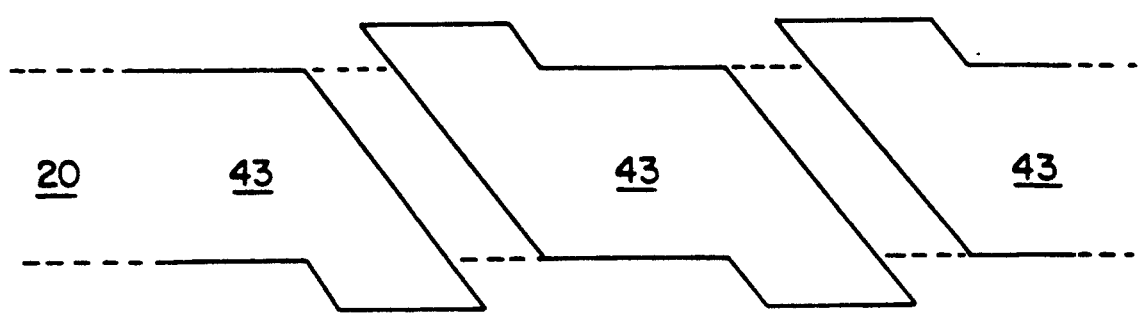

SLIT RADIOGRAPHY DEVICE PROVIDED WITH ABSORPTION ELEMENTS, AND PROCEDURE FOR PRODUCING ABSORPTION ELEMENTS

This is a division of application Ser. No. 07/852,682 filed Mar. 17, 1992 abandoned which is a continuation of Ser. No. 07/613,498 filed Oct. 31, 1990 now U.S. Pat. No. 5,134,642.

The invention relates to a slit radiography device, comprising an X-ray source which is capable, when in operation, of scanning a body under examination, via a slit of a slit diaphragm, with a fan-shaped X-ray beam in a direction transverse to the longitudinal direction of the slit, an absorption device comprising a number of movable absorption elements placed next to each other being provided, which absorption elements can be moved into the fan-shaped X-ray beam to a greater or lesser extent under the influence of suitable control signals in order to influence, when in operation, the X-ray radiation incident on the body per sector of the X-ray beam.

A device of the type described above is, for example, known from U.S. Pat. No. 4,715,056. U.S. Pat. No. 4,715,056 shows and describes diverse types of absorption elements which can be moved up and down in order to influence a fan-shaped X-ray beam, transmitted or to be transmitted through the slit of a slit diaphragm, per sector thereof. The absorption elements may be composed of small plates, situated next to each other, of material which attenuates or even completely absorbs X-ray radiation, which small plates are placed on the free ends of cantilever-mounted tongue-shaped devices. The tongue-shaped devices may advantageously be piezoelectric tongues, it being possible to control the position of the free ends, and consequently of the absorption elements, directly by electrical signals. Tongue-shaped devices controlled in a different manner may also be used, however, as can, for example, diverse types of means which are able to cause the absorption elements to perform a rectilinear to-and-fro sliding movement.

In all cases it is important that the absorption elements can be moved independently of each other in a direction transverse to the longitudinal direction of the slit of the slit diaphragm. Furthermore, adjacent absorption elements should adjoin each other in a manner such that the X-ray radiation cannot pass freely between two elements.

The absorption elements with rectangular cross section shown in U.S. Pat. No. 4,715,056 are only able to satisfy this last requirement if adjacent elements are situated so as to fit tightly against each other. However, this adversely affects the free movement capability. The trapezoidal elements and the elements provided with tongue and groove also shown in U.S. Pat. No. 4,715,056 can indeed be fitted with a small gap without X-ray radiation being able to pass freely between two adjacent elements. However, the radiation is then not absorbed to the same extent in the region of the edge parts of the elements which overlap each other as it is by the central part of the elements. This may produce strip-like artefacts in a radiograph to be made, which is undesirable.

The applicant has carried out an investigation into a slit radiography apparatus provided with an absorption device which is constructed with tongue-shaped elements which are provided at the free end with small plates of material, which absorbs X-ray radiation, placed transversely to the longitudinal direction of the tongues. In this case, the tongues were alternately relatively short and relatively long and the small plates of absorbing material were chosen so wide that adjacent small plates, which are consequently situated at different distances from the X-ray source, overlap each other to some extent. A drawback of this arrangement is, however, that the overlapping parts of the small plates give rise to strip-like artefacts in the radiographs to be made. The varying distances of the small plates from the X-ray source also result in a varying influencing of the X-ray beam with positions of the small plates which are otherwise identical.

The object of the invention is to eliminate the drawbacks outlined and to provide, in general, a slit radiography apparatus having an advantageous absorption device.

For this purpose, an apparatus of the type described is characterized, according to the invention, in that at least the edge sections facing each other of adjacent absorption elements are of matching construction and, viewed from the X-ray source, overlap each other, the edge section of an absorption element which, seen from the X-ray source, overlaps an edge section of an adjacent absorption element always being a small distance nearer the X-ray source than the matchingly constructed edge section of the other absorption element and the total material thickness at the site of the overlapping edge sections being equal to the material thickness between the edge sections.

A procedure for producing absorption elements for an absorption device of a slit radiography apparatus is characterized according to the invention in that the shape of the absorption elements is constructed by defining, between two equidistant lines which have a mutual spacing which is equal to the desired absorption thickness of the material to be used for the elements, at least two cut lines extending, at least not over the entire length, transversely to the equidistant lines; by defining, on either side of each cut line, two edge regions, which are each bounded by the cut line, a boundary line extending transversely to the equidistant lines and a part of at least one of the equidistant lines; by moving the edge regions thus determined on either side of each cut line over a small distance in opposite directions along the boundary lines, with the result that a gap is produced at the position of each cut line; and by using the shape situated between two gaps thus obtained as a template for the cross section of the absorption elements.

The invention will be explained in more detail below with reference to the accompanying drawing.

Figure 2:
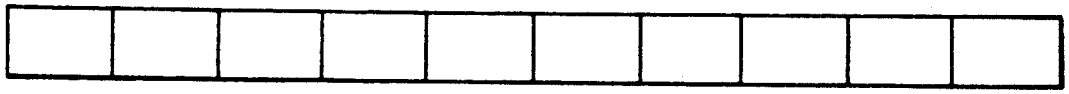
Figure 3:
Figure 4:
Figure 5:
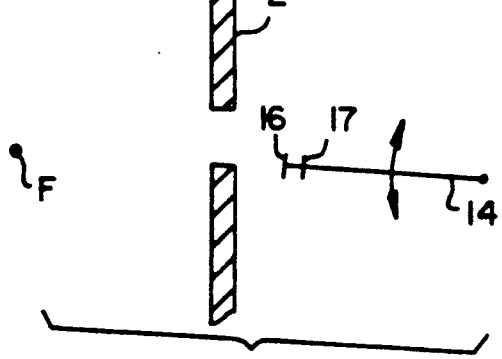
Figure 6:
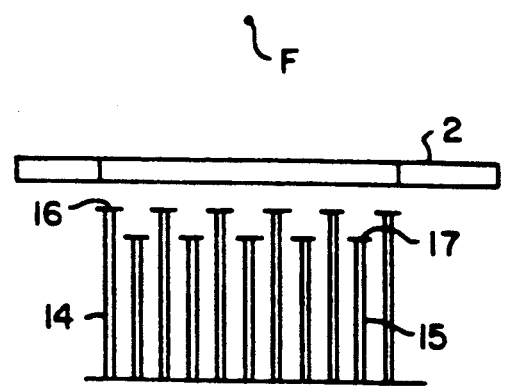
Figure 10A:
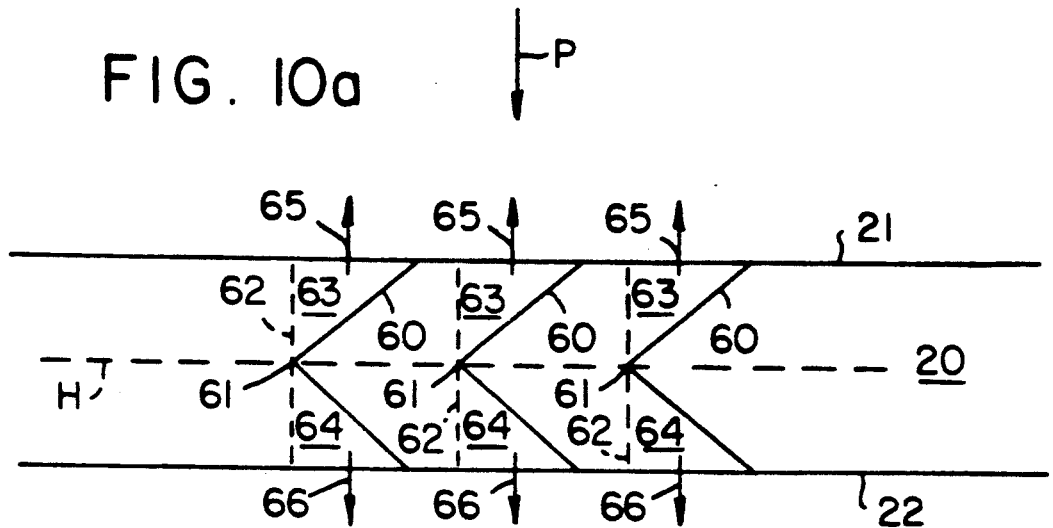
Figure 10B:
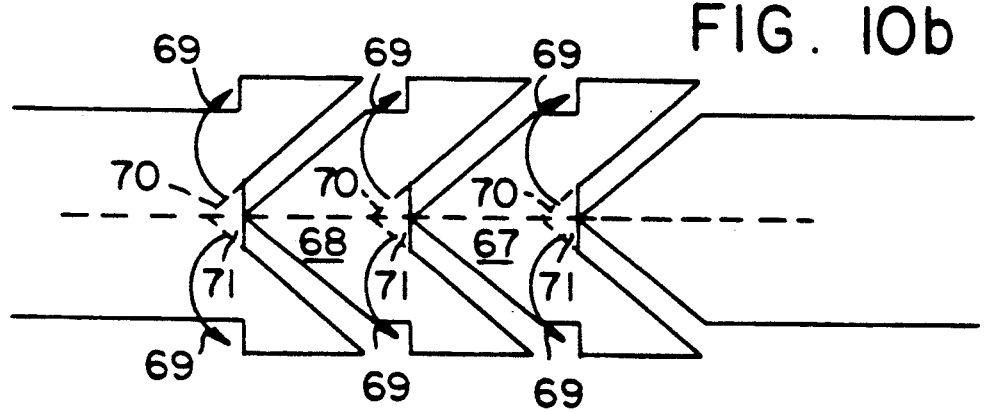
Figure 10C:
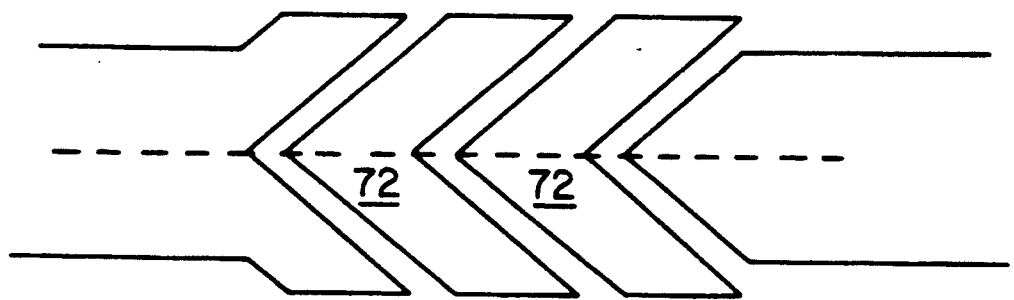
Figure 11:
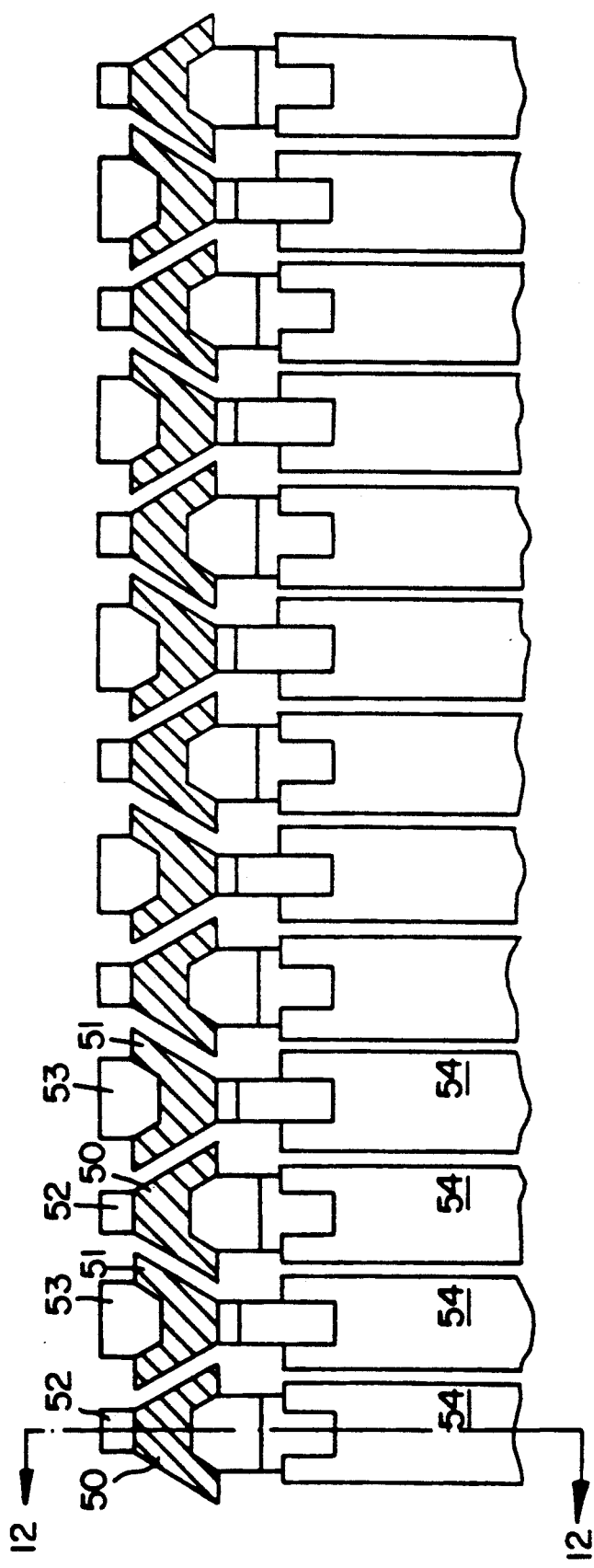
Figure 12:
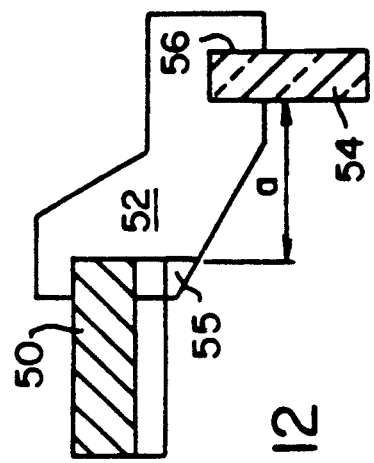

FIG. 1 diagrammatically shows an example of a slit radiography apparatus in side elevation;

FIGS. 2 to 4 inclusive diagrammatically show some examples of a number of absorption elements according to the prior art sited next to each other in plan view;

FIGS. 5 and 6 diagrammatically show an absorption device having tongues of alternatingly different length provided with small plates of absorbing material in side elevation and plan view respectively;

FIGS. 7a, 7b, 7c and 7d diagrammatically illustrate the basic idea of the invention;

FIGS. 8a, 8b, 8c, 9, 10a, 10b, 10c and 11 diagrammatically show examples of absorption elements for an apparatus according to the invention; and FIG. 12 shows a section along the line XII—XII in FIG. 11.

FIG. 1 diagrammatically shows an example of a slit radiography apparatus in side elevation. The apparatus shown comprises an X-ray source 1 having an X-ray focus F. Sited in front of the X-ray source is a slit diaphragm 2, with the aid of which a relatively flat, fan-shaped X-ray beam 3 is formed which is directed at an X-ray detector 4. As shown in FIG. 1, the X-ray beam 3 is in fact somewhat wedge-shaped in side elevation, but the height is small at the site of the X-ray detector, for example 3 cm, whereas the width of the beam perpendicular to the plane of the drawing may be, for example, 40 cm, with the result that the X-ray beam is, in general, said to be flat.

The X-ray source and the slit diaphragm may be moved together in a manner such that the X-ray beam performs a scanning movement transversely to the width direction of the beam, that is to say, vertically in the plane of the drawing, as indicated by a double arrow 5. Such a scanning movement can be achieved in a simple manner by causing the assembly comprising X-ray source and slit diaphragm to swivel about an axis extending transversely to the plane of the drawing through the X-ray focus F, as indicated by an arrow 6. A flat, fanshaped beam which performs a scanning movement may, however, also be obtained in another manner, such as that indicated, for example, in U.S. Pat. No. 4,715,056.

The X-ray detector 4 in the example shown is a standard large-film cassette which is exposed stripwise in the vertical direction during the scanning movement of the X-ray beam. Instead of such a stationary large-image cassette, use could also be made of a strip-type X-ray detector which converts the instant X-ray radiation into a strip-type light image which is in turn used to expose a photographic film. An example of such a use of a strip-type X-ray detector is also shown in the U.S. Pat. No. 4,715,056.

In order to be able to regulate the amount of X-ray radiation which is directed at a patient or object under examination 7 at a particular instant and in a particular sector of the X-ray beam, which also regulates the exposure of the corresponding section of the X-ray detector, an X-ray absorption device 8 is sited in the X-ray beam near the slit diaphragm 2. The absorption device is so constructed that, under the influence of suitable regulation signals, it is possible to regulate the amount of radiation transmitted per sector of the X-ray beam at any instant.

Some examples of absorption devices are described in U.S. Pat. No. 4,715,056.

The regulating signals for the absorption device are provided by a regulating circuit 10. The regulating circuit 10 receives input signals from a detection device 11 which detects the amount of X-ray radiation transmitted through the patient or the object 7 instantaneously per sector of the fan-shaped X-ray beam and emits corresponding electrical output signals.

The detection device may be situated between the patient or the object and the X-ray detector 4 as shown in FIG. 1, but it may also in principle be situated behind the X-ray detector 4. In both cases, the detection device may respond either directly to incident X-ray radiation or to light radiation generated by the X-ray detector 4 in response to incident X-ray radiation.

If the detection device is situated between the patient or the object 7 and the X-ray detector 4, it is advisable for the detection device to be as transparent as possible to X-ray radiation so that the final X-ray image should be influenced as little as possible by the detection device. Suitable detection devices are, for example, described in the Dutch Patent Application 8503152 and in the Dutch Patent Application 8503153.

FIGS. 2 to 4 inclusive diagrammatically show, in plan view, some examples of absorption elements, sited next to each other in accordance with the prior art, of an absorption device for a slit radiography apparatus. The elements shown may be fitted, for example, on the free ends of cantilever-mounted tongues, the angular position of which can be controlled by the regulating circuit 10 independently of the position of the other tongues. In this way, the absorption elements can be introduced into the X-ray beam to a greater or lesser extent independently of each other.

The absorption elements may also be coupled to other types of drive devices which make an upward or downward sliding movement possible in order to introduce the elements into the X-ray beam to a greater or lesser extent independently of each other.

It is advisable for the elements shown in FIG. 2 to be situated very close to each other because otherwise slits are produced between adjacent elements, which slits transmit the X-ray radiation freely. This produces strip-type artefacts in the radiograph to be made. However, it is difficult to construct such elements which are sited close to each other so as to be independently movable.

In the absorption elements shown in FIGS. 3 and 4, adjacent elements have matchingly shaped parts which enmesh and/or partially overlap each other. As a result, these elements can be used with a small space between adjacent elements without the X-ray radiation being able to pass freely between adjacent elements. The overlapping parts of adjacent elements absorb the X-ray radiation, albeit to a lesser extent, as a result of which strip-type artefacts are produced in the radiograph to be made.

FIGS. 5 and 6 diagrammatically show an example of an absorption device having piezoelectric tongues 14, 15 which are alternately shorter and longer and which each support, at the free end, a small plate 16 or 17 respectively of material which absorbs X-ray radiation. As can be seen in FIG. 6, the small plates overlap each other to some extent, as a result of which strip-type artefacts may also be produced. The distance between the small plates 16 and the X-ray focus F also differs from that between the small plates 17 and the X-ray focus F, with the result that the small plates 16 and the small plates 17 do not influence the associated sectors of the X-ray beam in the same manner.

According to the invention, the drawbacks outlined above are eliminated by forming, in the following manner, an assembly of absorption elements situated next to each other from an elongated strip of absorption material having a rectangular cross section and having a length which is equal to the total length of the absorption elements, situated next to each other, of the desired absorption device. A number of cuts are made in the strip such that a number of sections corresponding to the desired number of absorption elements is produced. Said cuts may be arbitrary in shape but not parallel, at least not over the entire length, to the direction of the X-ray radiation to be attenuated. Furthermore, in view of the geometry of the rest of the slit radiography apparatus, the cuts are preferably made in a manner such that the sections obtained are of identical shape. Then the edge parts, situated on either side of a cut, of each pair of adjacent sections are moved in the direction of the X-ray source or in the opposite direction respectively.

All this is illustrated diagrammatically in FIG. 7. FIG. 7 diagrammatically shows, in plan view, a strip 20 of material which absorbs X-ray radiation. The direction of the X-ray radiation to be influenced in the final operating condition is indicated by an arrow P. In plan view, the strip 20 has two equidistant longitudinal edges 21, 22, of which, in the operating condition, one faces the X-ray source and the other faces away from the X-ray source. In the example shown the equidistant longitudinal edges from parallel straight lines. However, the longitudinal edges may also be curved. Advantageously, the longitudinal edges may form parts of concentric circles whose common centre point coincides in the assembled condition of the absorption elements with the X-ray focus of the X-ray source. An arbitrary cut line 25 has been made between an arbitrary point 23 on the first edge 21 and a point 24 arbitrarily situated, but not situated in the projection of point 23 in the direction of the arrow P, on the second edge 22. The cut line therefore divides the strip 20 into two parts 20a and 20b. The part, adjacent to the cut line 25, of the part 20a of the strip is now moved through a predetermined distance x in the direction of the X-ray source, while a preferably equally large part of a part 20 is moved through the same distance x in the opposite direction. All this is shown in FIG. 7b.

Figure 7A:
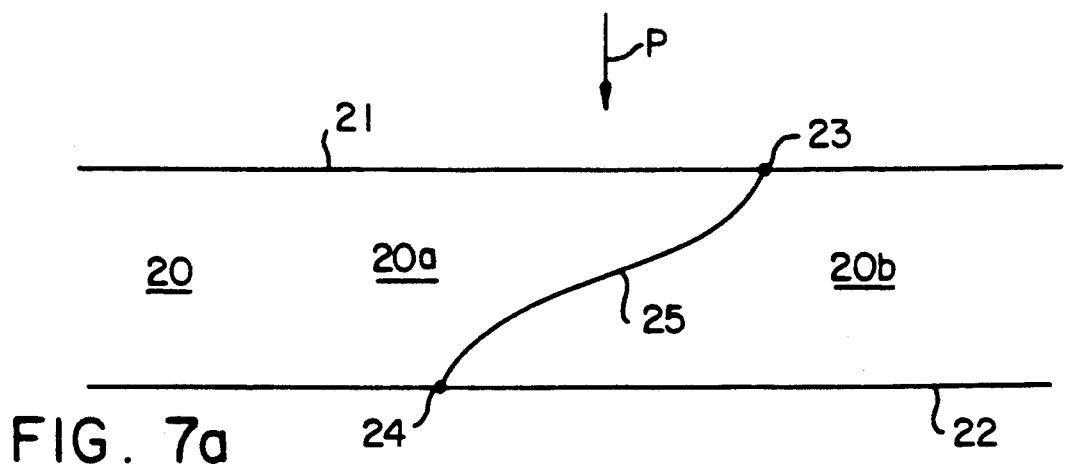
Figure 7B:
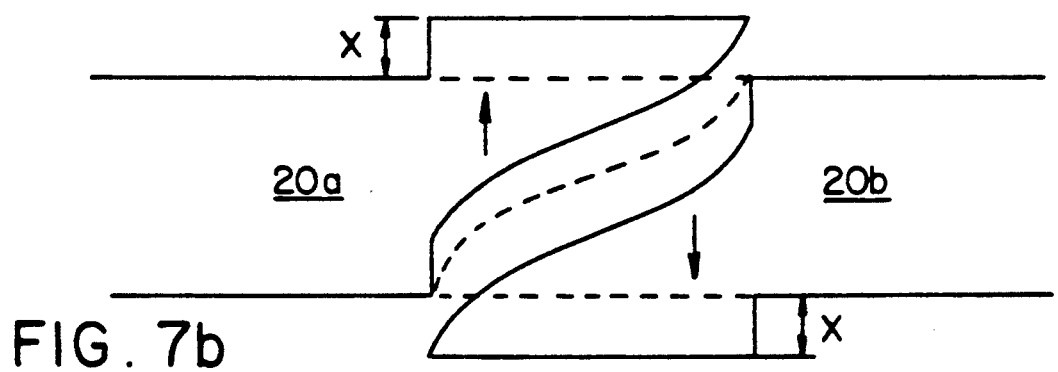

In FIG. 7b it can be seen that the parts 20a and 20b still jointly influence, in the same manner, X-ray radiation which is incident along the arrow P, but that at the same time, a space 2x is created between the two parts, as a result of which the parts are able to move transversely to the plane of the drawing independently of each other and without mutual friction. The average distance from the X-ray source has also remained unaltered in the region of the parts moved.

The desired absorption elements are formed by carrying out the same operation at other sites along the strip 20. It is pointed out that, in principle, a differently shaped cut line can be chosen for every cut and that the different sections do not have to be equally long.

From the point of view of symmetry and of adaptation to the geometry of the rest of the slit radiography apparatus, and also with a view to as simple a production technique as possible, however, identically shaped sections and, consequently, also identically shaped absorption elements are preferably formed.

Figure 7C:
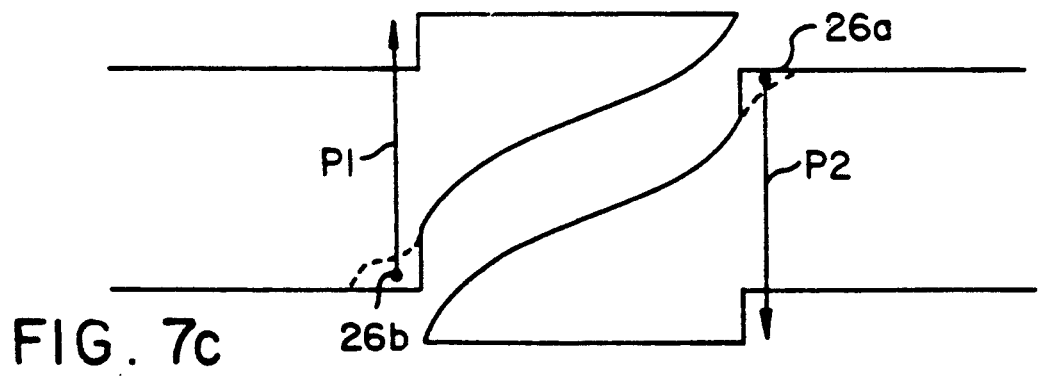
Figure 7D:
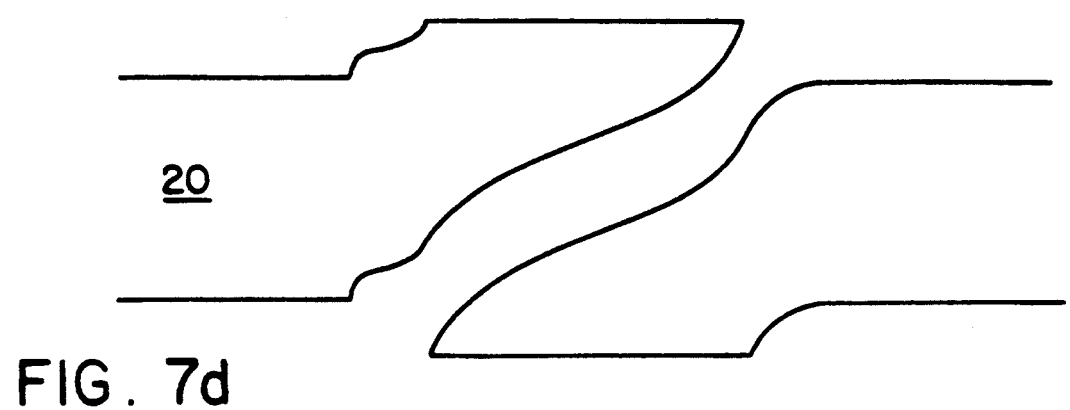

FIG. 7c further shows how the sharp corners still present in FIG. 7b can be avoided. For this purpose, the parts 26a and 26b, of which the original points 23 and 24 form the vertices, are displaced towards the oppositely situated edges of the strip 20, as indicated by arrows P1 and P2. It can be seen that the parts 26a and 26b are not of identical shape. Preferably, these parts are, however, in fact of identical shape. The result of this operation can be seen in FIG. 7d.

It is pointed out that the cut line 25 is preferably a line which has essentially the same direction over the entire path between the points 23 and 24. Nevertheless, in a particular situation, the line 25 may have one or more undercuts or points of inflection. In some cases, it may be possible to use a kinked cut line between two points situated directly opposite each other, but in that case it is advisable for one half of one and the same strip section to be moved in one direction and the other half in the opposite direction. No part of the other strip section then needs to be moved.

A practical example of the method described above is illustrated in FIG. 8 which shows the shaping of essentially trapezoidal absorption elements whose long and short parallel sides alternately face the X-ray source which is not shown.

In a similar manner, FIG. 9 illustrates an example of essentially parallelogram-shaped absorption elements.

FIG. 10 shows an example in which the cut line is a kinked cut line between two points situated directly opposite each other.

FIG. 8 again shows, in part A, a strip of material 20 on which cut lines 30, 31 are indicated which divide the strip into trapezoidal parts. Trapezoidal parts situated next to each other are oppositely directed with respect to the X-ray radiation, which is indicated by an arrow P.

Parts of the strip adjacent to the cut lines are indicated by broken lines 32, 33. These parts are moved according to the arrows 34 and 35 respectively in the direction of the X-ray radiation and oppositely thereto respectively. The result of the operation is shown by FIG. 8B. FIG. 8C shows the result of a further operation which corresponds to the operation indicated in FIG. 7C.

The absorption elements 40, 41 obtained are essentially trapezoidal but may change into triangular shapes if the lines 30, 31 are closer together.

It is pointed out that the broken lines 32, 33 which bound the parts to be moved do not necessarily have to emerge at the intersections of the cut lines 30, 31 with the front and rear edge of the strip of material. The broken lines may be situated further apart or even closer together than is indicated in FIG. 7 and FIG. 8.

FIG. 9 shows the result of the operations indicated in FIGS. 7 and 8 if all the cut lines 25 or 30, 31 are chosen parallel. The absorption elements 43 are now essentially parallelogram-shaped.

It is pointed out that, in principle, the parts to be moved in the direction of the X-ray radiation or in the opposite direction respectively could be so large that the entire region between two cut lines is moved. In the example of FIG. 8, the trapezoidal parts of FIG. 8A could be alternately moved in one direction or the other direction. In the example of FIG. 9, the parallelogram-shape parts may be divided into groups of three elements, of which the central one is not moved and the outer two are moved in opposite directions. Such a technique may, however, be subject to the drawback that the differences in distance between the X-ray source and adjacent elements result in excessively large differences in the effect on the X-ray beam. This drawback does not occur, or barely occurs, in the techniques illustrated in FIGS. 7 to 9 inclusive because only small parts of each element are moved.

It is furthermore pointed out that the method described above has to be regarded, insofar as the moving of parts of elements is mentioned, as a design technique. After the shape and dimensions of the absorption elements to be produced, and also the position of adjacent elements with respect to each other, have been determined in the manner described, the elements themselves can be produced in any manner suitable therefor and mounted in an absorption device.

It is pointed out that the shape of the absorption elements can be most precisely constructed by starting from a strip of material which is curved according to a circular arc having a radius which corresponds to the distance between the X-ray focus of the X-ray source and the absorption elements in the slit radiography apparatus for which the elements are intended. The edges 21, 22 of FIG. 7 and FIG. 8 then form concentrically curved lines and the boundary lines are then parts of radial lines originating from the X-ray focus of the apparatus to be produced or lines extending transversely to the curved lines.

To a good approximation it is possible in practice to start from a straight strip whose edges 21, 22 form parallel lines and for which all the boundary lines 32, 33 are parallel to each other and consequently again extend transversely to the edges 21, 22. The absorption elements produced in this way are then installed in the slit radiography apparatus along a circular arc corresponding to the distance from the X-ray focus of the X-ray source.

FIG. 10 again shows a strip 20 having equidistant longitudinal edges 21, 22, the direction of the X-ray radiation with respect to the absorption elements to be formed once they have been mounted in a slit radiography apparatus being indicated by an arrow P. In the strip 20 there are drawn, as an example, three cut lines 60 which, in contrast to the cut lines 25 and 30, 31, are kinked. In the example shown all the cut lines 60 are equidistant and the points of inflection 61 are situated precisely on the longitudinal centre line H of the strip 20. In addition, the intersections of each cut line with the edges 21, 22 of the strip 20 are precisely opposite each other viewed in the direction of the arrow P. The cut lines are consequently completely symmetrical with respect to the centre line H and they are also all identically oriented. This is, however, by no means necessary.

FIG. 10A furthermore also indicates by means of broken lines boundary lines 62 which are parallel to the arrow P, that is to say to the direction of the X-ray radiation prevailing on the spot in a practical situation.

Together with the kinked line and the two edges 20, 21, each boundary line now always includes two triangular regions 63, 64.

It is pointed out that the boundary lines may also be situated more to the left or to the right with respect to the point of inflection, with the result that two quadrangular regions or smaller triangular regions are produced. In the figure it can be seen that the regions 63 can now be moved against the direction of the arrow P, while the regions 64 can be moved in the direction of the arrow P. These directions of movement are indicated for the individual regions by arrows 65, 66. After performing the movements, the result shown in FIG. 10B is obtained. Since the adjacent elements 67, 68 still make contact with each other at the position of the original point of inflection 61, the inside edges of the elements formed are continued until they intersect each other, which is the case in the example shown at the position of the longitudinal centre line H of the original strip 20. On either side of the longitudinal centre line, triangular sections 70, 71 are then produced which are displaced in the manner indicated by the curved arrows 69 to the longitudinal edges 21, 22 and exactly fill in at that point a recess produced by the outward movements.

In this way, the chevron-shaped elements 72 shown in FIG. 10C are produced. Like the trapezoidal elements constructed by the method of FIG. 8, such chevron-shaped elements are also very suitable for manufacture in large numbers, while the mounting is very simple and identical for all the elements.

FIG. 11 shows, in plan view, a part of an absorption device provided with absorption elements 50, 51 of the type shown in FIG. 8. FIG. 12 shows a cross section along the line XI—XI in FIG. 11.

All the absorption elements used are identical but the wide side or the narrow side respectively alternately face the X-ray source. It can be seen that the absorption elements of FIG. 10 are entirely situated on one line. This situation can be achieved in a simple manner starting from the situation shown in FIG. 8 by, for example, displacing the elements 41 in the direction of the arrow P in FIG. 8C. The elements in that case remain free of each other by the operation symbolized in FIG. 8B by the curved arrows.

In the embodiment of FIGS. 11 and 12, the absorption elements are mounted upright on carriers 52, 53, for example by gluing. The carriers are in turn mounted on the ends of tongue-like devices 54, for example piezoelectric tongues. The carriers are produced from material transparent to X-ray radiation and are preferably provided with a recess 55 which can at least partially receive one of the end faces of an absorption element. A rigid mounting and precise positioning of the elements is promoted in this way.

Furthermore, each of the carriers is provided with a second recess 56 which grips around the end of an associated tongue. The carriers are shaped in a manner such that the absorption elements are situated at a distance from the tongues viewed in the direction of movement. This distance a (FIG. 12) is preferably at least as great as the maximum stroke which the end of the tongue can perform in operation, with the result that the tongues themselves remain outside of the X-ray beam.

The absorption elements described and shown have as an additional advantage that the absorption gradually decreases to zero for X-ray radiation at the two ends of each element. This is of importance in the case where, for example, an absorption element extends further into the X-ray beam than the adjacent elements. A gradual decrease in the absorption avoids artefacts in the radiograph to be formed.

It is pointed out that, after the above, diverse modifications of the examples described are obvious to the person skilled in the art. Thus, the number of possible shapes of the absorption elements is, in principle, unlimited because both the position of the points between which the cut lines 25; 30, 31; 60 extend and the path of the cut lines between said points, and also the position of the boundary lines may, in principle, be varied in an infinite number of ways. Only a few examples have been described above.

Furthermore, after the shape of the individual elements has been determined in the manner described, they can be advantageously produced from a composite material whose components have overlapping K shells. The elements may, for example, be produced from a strip of laminated material which contains one or more layers of tantalum and/or lead and/or tungsten. Such a strip of material may, for example, be composed of a central layer of tantalum which is clad on both sides with a layer of lead. In this manner, absorption elements having a relatively large absorption for X-ray radiation can be obtained. Such modifications are considered to fall within the scope of the invention.

We claim:

1. A method for producing absorptione elements for a slit radiography assembly, which comprises:

forming a template of a cross-sectional shape for said absorption elements by defining at least two cut lines between two equidistant lines of absorption thickness of absorption material, said cut lines being non perpendicularly transverse to said equidistant lines; by defining two edge regions with a boundary line on either side of each cut line, each of said edge regions being bounded by said cut lines, said boundary line extending transversely to said equidistant lines and a part of at least one of said equidistant lines; and by moving said edge regions on either side of each said cut lines a distance in an opposite direction along said boundary lines to produce a gap at a position of each of said cut lines thereby forming said cross-sectional shape between respective gaps; and forming an absorption element of said cross-sectional shape from said template.

2. The method for producing absorption elements as defined in claim 1 wherein straight shoulders produced by movement at the position of said boundary lines are chamfered by displacing a projecting angular section near one equidistant line to an oppositely situated angular section near the other equidistant line.

3. The method for producing absorption elements as defined in claim 1 wherein at least one of said cut lines is kinked having a first section extending between an intersection thereof with one of said equidistant lines and a point of inflection and having a second section extending between said point of inflection and a second of said equidistant lines and wherein said boundary line is drawn transversely through said point of inflection and wherein a region formed by said boundary line, said first section and a part of a first of said equidistant lines is moved in a first direction transversely to said equidistant lines and wherein a region formed by said boundary line, said second section and a second of said equidistant lines is moved in said opposite direction and the thus-produced projecting corners at a position of said intersection of said boundary line with said equidistant lines is filled by triangular sections removed at the level of the original point of inflection.

* * * * *

UNITED STATES PATENT AND TRADEMARK OFFICE
CERTIFICATE OF CORRECTION

PATENT NO. : 5,257,305

DATED : OCTOBER 26, 1993

INVENTOR(S) : HENDRIK J. VAN ELBURG ET AL.

It is certified that error appears in the above-identified patent and that said Letters Patent is hereby corrected as shown below:

On the title page, Item [73]:
 ASSIGNEE: B.V. OPTISCHE INDUSTRIE "DE OUDE DELFT"

Signed and Sealed this

Twelfth Day of April, 1994

Attest:

BRUCE LEHMAN

Attesting Officer  Commissioner of Patents and Trademarks